(12) United States Patent
Chawla

(10) Patent No.: US 7,281,539 B2
(45) Date of Patent: Oct. 16, 2007

(54) MEDICAMENT CONTAINER

(75) Inventor: Brindra Paul Singh Chawla, Nottingham (GB)

(73) Assignee: Technology Innovation Limited, Nottingham (GB)

( * ) Notice: Subject to any disclaimer, the term of this patent is extended or adjusted under 35 U.S.C. 154(b) by 273 days.

(21) Appl. No.: 10/474,386

(22) PCT Filed: Apr. 12, 2002

(86) PCT No.: PCT/GB02/01728

§ 371 (c)(1),
(2), (4) Date: Oct. 9, 2003

(87) PCT Pub. No.: WO02/085281

PCT Pub. Date: Oct. 31, 2002

(65) Prior Publication Data

US 2004/0129268 A1    Jul. 8, 2004

(30) Foreign Application Priority Data

Apr. 19, 2001  (GB) ................................ 0109693.2
Jan. 3, 2002   (GB) ................................ 0200063.6

(51) Int. Cl.
    *A61M 15/00*  (2006.01)
(52) U.S. Cl. .................. 128/203.15; 128/203.21; 128/203.19; 604/58; 220/302
(58) Field of Classification Search .......... 128/203.12, 128/203.15, 203.21–203.23, 204.13, 204.14, 128/203.19, 206.11, 205.21, 204.11, 204.12; 222/129, 142, 1, 142.2, 142.6, 142.7, 142.8, 222/143; 215/307, 309; 220/367.1, 4.26, 220/4.27, 676, 521, 302; 206/528, 535, 536; 366/234, 130; 604/58
See application file for complete search history.

(56) References Cited

U.S. PATENT DOCUMENTS

| 3,899,121 | A  | * | 8/1975  | Herbetko ............... 206/509 |
| 5,301,666 | A  | * | 4/1994  | Lerk et al. ............ 128/203.15 |
| 5,524,613 | A  |   | 6/1996  | Haber et al. |
| 5,778,873 | A  |   | 7/1998  | Braithwaite |
| 5,934,515 | A  | * | 8/1999  | Bennett ............... 222/153.14 |
| 6,328,034 | B1 | * | 12/2001 | Eisele et al. .......... 128/203.15 |
| 6,418,926 | B1 | * | 7/2002  | Chawla ............... 128/203.12 |
| 6,810,873 | B1 | * | 11/2004 | Haikarainen et al. .. 128/203.15 |
| 7,219,665 | B1 | * | 5/2007  | Braithwaite ........... 128/203.21 |

FOREIGN PATENT DOCUMENTS

| FI | 990913      | * 4/1999 | ......... 128/203.15 |
| WO | WO9216249 A1 | 10/1992 | |
| WO | WO9516483 A1 | 6/1995  | |
| WO | WO9826828 A1 | 6/1998  | |
| WO | WO 00/35522 | 6/2000  | |

* cited by examiner

Primary Examiner—Justine R. Yu
Assistant Examiner—Shumaya B. Ali
(74) Attorney, Agent, or Firm—Nixon Peabody LLP

(57) ABSTRACT

A medicament container (10) is disclosed which comprises at least two compartments (21, 22). Each of the compartments (21, 22) is adapted to contain a dose of a medicament in powdered form and is provided with at least one opening (23) through which, in use, the medicament can be dispensed. The container (10) is preferably cylindrical in form, the diameter of the cylinder being greater than its depth such that the container (10) has the form of a squat drum.

29 Claims, 3 Drawing Sheets

MEDICAMENT CONTAINER

This application is a national stage application under 35 U.S.C. §371 from PCT Application No. PCT/GB02/01728 filed Apr. 12, 2002, which claims the priority benefit of Great Britain Application No. 0109693.2 filed Apr. 19, 2001 and Great Britain Application No. 0200063.6 filed Jan. 3, 2002.

This invention relates to a medicament container, in particular to a container adapted to contain a plurality of unit doses of one or more powdered solid medicaments intended for administration by inhalation, and to a method of administration of such medicaments from such a container.

The administration of medicaments by inhalation is well known. Such medicaments are often administered in the form of solid powders. Pressurised metered dose inhalers (MDI's) are one well-known form of administration, but concerns about the environmental effects of the propellants used in such systems has lead to increased attention on so-called dry powder inhalers. In such inhalers, a dose of powdered medicament is entrained in a swirling airflow and inhaled, the swirling airflow normally being created by the act of inhalation.

One form of dry powder inhaler is described in International Patent Application WO 98/26828. This device utilises medicament containers having the form of squat drums which are held in a chamber and caused by the patient's inspiratory airflow to undergo an epicyclic motion. The containers have openings around their periphery through which the medicament is dispensed into the airflow and hence is inhaled by the patient.

In the treatment of diseases of the airways, or indeed other diseases that are treated by inhalation therapy, it is not unusual for two or more different medicaments to be prescribed. Most commonly, this involves the patient in the separate administration of the two different drugs, either taking one straight after the other or taking the two medicaments according to two different administration regimes. This can lead to errors, eg as a result of a patient administering to himself two doses of one medicament, rather than one dose of each of two medicaments. The resulting overdose of one drug, and underdose of the other, can seriously reduce the therapeutic benefit to the patient, or can even be dangerous to the patient.

There have now been devised novel forms of medicament container that are specifically adapted for the delivery of combinations of two (or more) different medicaments by inhalation.

According to the invention, there is provided a medicament container comprising at least two compartments, each of said compartments being adapted to contain a dose of a medicament in powdered form and each compartment being provided with at least one opening through which, in use, said medicament can be dispensed.

The medicament container according to the invention is advantageous primarily in that it permits the simultaneous administration of more than one medicament and thereby reduces the risk of mis-administration of two medicaments, in particular reducing the risk that the medicaments may be administered in the wrong ratios. Since the two medicaments are dispensed simultaneously, they are intimately mixed during administration and are therefore delivered to the target tissue, eg the patient's lungs or nasal cavity, simultaneously and with equal efficiency.

The container according to the invention most preferably has a circular or substantially circular cross-section, the diameter of the circle being greater than the depth of the container. Such a shape is particularly suitable for use in devices of the type disclosed in WO 98/26828. Containers of such a form may be generally cylindrical in shape. At least one end of the cylindrical container is preferably substantially flat, such that in use the container may rest upon that end. In such a case, the container has the form of a squat drum. However, one or both ends of the cylinder may be somewhat convex (or concave). The shape may therefore be discus-like.

The compartments are most preferably disposed one above the other, along the longitudinal axis of a cylindrical or similar container. However, other arrangements may also be employed, eg a plurality of compartments arranged as segments of a cylindrical disc. The container may, for instance; take the form of a squat cylindrical drum divided by a diametral wall into two hemicylindrical compartments.

The dispensing apertures are preferably formed around the periphery of the compartments. Most preferably, there are a plurality of such apertures in each compartment, preferably equiangularly spaced around the wall of the compartment.

The dispensing apertures may all be of equal size. Alternatively, the dispensing apertures in different compartments may be of different sizes. This may lead to differences in the rate of delivery of the medicaments from the compartments into the airstream that is inhaled. For example, relatively large apertures in one compartment may lead to very rapid emptying of a first medicament from that compartment, while relatively small apertures in another compartment may lead to slower release of another medicament from that compartment.

When used in systems such as those disclosed in WO 98/26828, the container is caused to undergo an epicyclic motion, in which it orbits within a swirl chamber and simultaneously rotates about its own axis.

The container is preferably manufactured from materials that are impermeable or substantially impermeable to moisture.

The container most commonly comprises two compartments, adapted to receive doses of two different medicaments. However, more than two compartments may be present, and references herein to the use of the container to administer two different medicaments should be understood to encompass the possibility that more than two medicaments may be involved. It will also be apparent that more than one compartment may be filled with the same medicament. The container may therefore be used to administer different total dosages of a single medicament, depending on the number of compartments that are filled, or two or more medicaments may be filled separately into some or all of a larger number of compartments, thereby allowing some variation in the ratio of the medicaments that are administered. In another alternative, two or more compartments may be charged with the same medicament, but formulated differently, eg for delivery to different regions of the target tissue. For instance, different compartments may contain a medicament in forms having different particle size distributions.

Examples of combinations of medicaments that may be incorporated into separate compartments of a medicament container according to the invention are:

Bronchodilators ($\beta_2$-agonists) and steroids, eg
formoterol and budesonide
salmeterol and fluticasone
formoterol and fluticasone
salmeterol and budesonide
Anticholinergics and steroids, eg ipratropium bromide and budesonide
ipratropium bromide and fluticasone
oxitropium bromide and budesonide
oxitropium bromide and fluticasone Non-steroidal anti-inflammatory drugs (NSAIDs) and steroids or anti-cholinergics, eg
sodium cromoglycate and budesonide
sodium cromoglycate and fluticasone
sodium cromoglycate and ipratropium bromide
sodium cromoglycate and oxitropium bromide
nedocromil sodium and budesonide
nedocromil sodium and fluticasone
nedocromil sodium and ipratropium bromide
nedocromil sodium and oxitropium bromide Normal-acting and long-acting formulations of the same active ingredient, eg proteins and peptides, for instance insulin formulations for both fast and continued medication.

The container according to the invention is preferably supplied, pre-loaded with the medicaments that are to be administered, in packaging which seals the dispensing apertures until the container is removed from the packaging and introduced into the delivery device for use. Suitable forms of such packaging may include variations on the forms of packaging disclosed in WO 98/26828. Alternatively, one or more containers according to the invention may be pre-loaded into a medicament delivery device, again as disclosed in WO 98/26828, the device being intended to be discarded after the last of the pre-loaded medicament containers has been used.

The invention will now be described in greater detail, by way of illustration only, with reference to the accompanying drawings, in which FIG. 1 is a perspective view of a first embodiment of a medicament container according to the invention;

Figure 1:
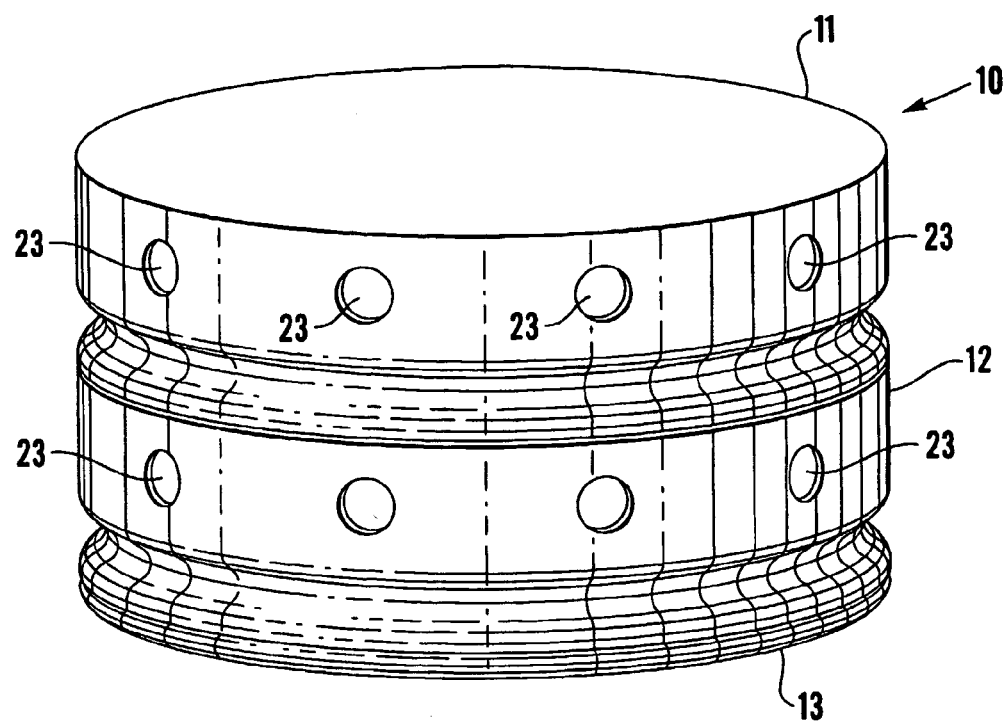

Referring first to FIG. 1, a first embodiment of a medicament container according to the invention is generally designated 10. The container 10 has the form of a relatively squat cylinder with a diameter of approximately 10 mm and a height of approximately 6 mm.

Figure 2:
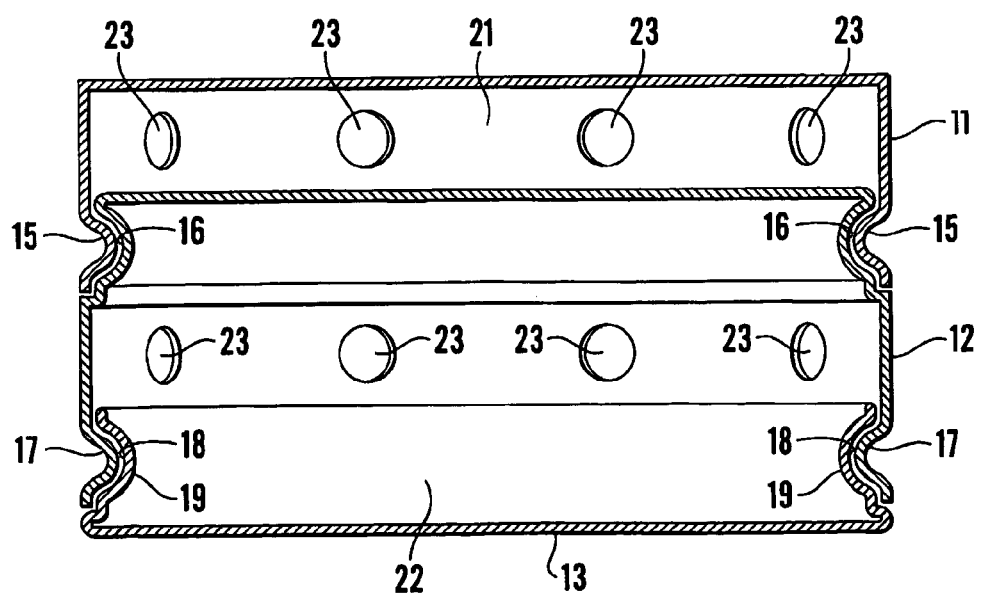
FIG. 2 is a sectional view of the container of FIG. 1.

The container 10 is assembled from three components, shown more clearly in FIG. 2. These are an upper compartment shell 11, a lower compartment shell 12 and a closure 13. All three components 11, 12, 13 are pressed from thin aluminium sheet. Alternatively, the components 11, 12, 13 may be formed in plastics material, eg by injection moulding.

The components 11, 12, 13 are fitted together so as to define upper and lower medicament compartments 21, 22, which are closed save for dispensing openings 23 that are provided at equiangularly spaced intervals in the wall of each of the compartments 21, 22. The openings 23 are disposed in planes approximately central to each of the respective compartments 21, 22.

Each of the upper and lower compartment shells 11, 12 take the form of open-mouthed cylinders. The upper compartment shell 11 is formed near its open base with an inwardly-projecting, annular rib 15 that engages a corresponding annular groove 16 formed near the top of the lower compartment shell 12. Likewise, the lower compartment shell 12 has an annular rib 17 formed near its base that cooperates with a groove 18 formed in an upstanding rim 19 around the periphery of the closure 13.

The container 10 is assembled by pressing the closed end of the lower compartment shell 12 into the open mouth of the upper compartment shell 11, such that the rib 15 engages in the groove 16. This closes the upper compartment shell 11. Similarly, the closure 13 is pressed into the open mouth of the lower compartment 12 such that the rib 17 engages in the groove 18, thereby closing the lower compartment shell 12.

In practice, the assembly process described above would also include the steps of filling a dose of medicament into each compartment. This may be facilitated by assembling the container 10 in an inverted condition. A dose of a first medicament is filled into the upper compartment shell 11, which is then closed by application of the lower compartment shell 12. A dose of a second medicament is then filled into the lower compartment shell 12, which is then closed by application of the closure 13.

It will generally be desirable for the openings 23 to be closed during the filling and assembly process. To achieve this, the assembly process may be carried out by fitting the components sequentially into a package in which the container is to be supplied, and which incorporates appropriate seals for the openings 23.

Figure 3:
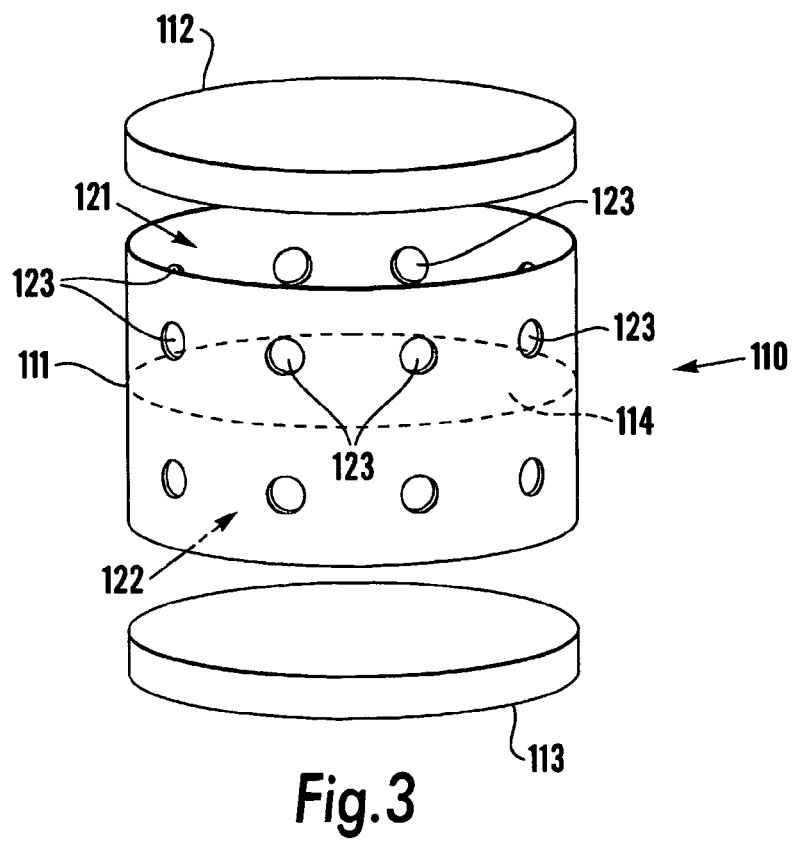
FIG. 3 is an exploded, sectional view of a second embodiment of a medicament container according to the invention.

FIG. 3 is an exploded, cross-sectional view of a second embodiment of a medicament container according to the invention, generally designated 110. This comprises three components, all of which are injection moulded in rigid, moisture-impermeable plastics material. The three components are a main body 111 and two identical closure caps 112, 113. The main body 111 is in the form of a cylinder which is open at both ends but has a central partition 114 that divides the body 111 into two compartments 121, 122. The dimensions of the body 111 are similar to the overall dimensions of the embodiment of FIGS. 1 and 2.

The open ends of the body 111 are closed by the respective closure caps 112, 113, each of which engages over the respective end of the body 111 with a tight interference fit.

As for the first embodiment, each compartment 121, 122 of the embodiment of FIG. 3 is formed with dispensing openings 123.

Figure 4:
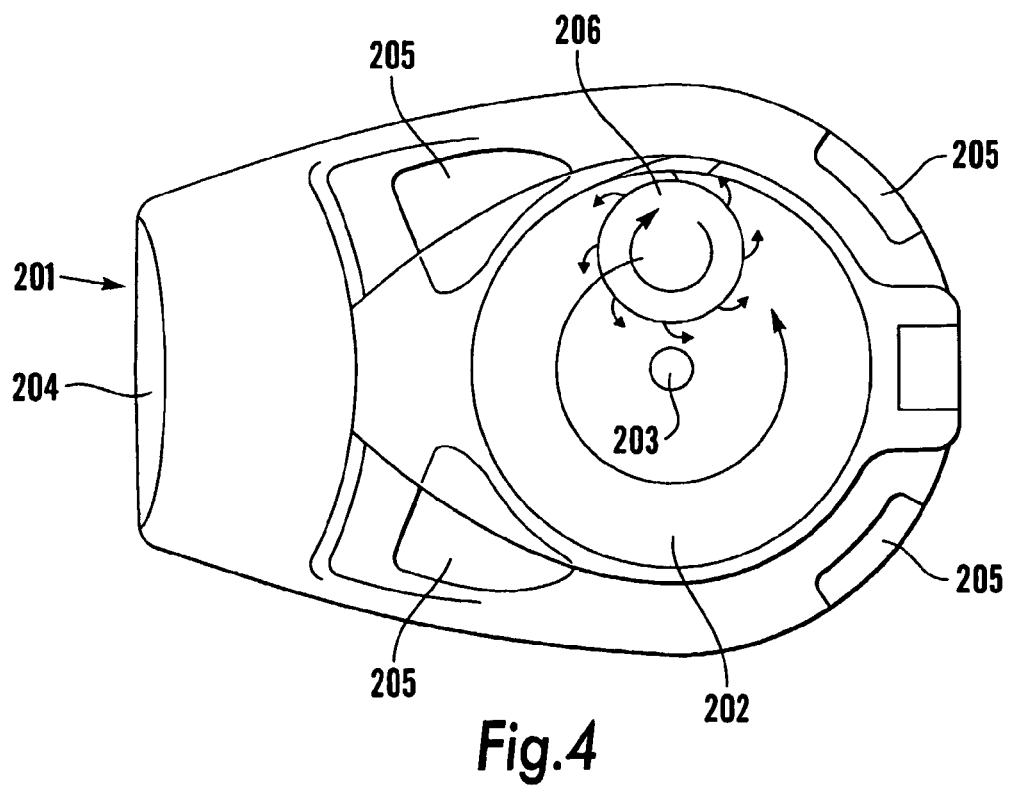
FIG. 4 is a plan view of a medicament inhaler device loaded with a medicament container according to the invention, showing the path of movement of the container during use.

FIG. 4 shows an inhaler device of the type disclosed in WO 98/26828. For the purposes of the present application, it is sufficient to note that the inhaler (generally designated 201) includes a swirl chamber 202 which is circular in form. A pillar 203 is present in the centre of the chamber 202.

The inhaler 201 has a mouthpiece 204 at which a patient can inhale. Such inhalation causes air to be drawn into the chamber 202 via air inlets 205. The arrangement of these inlets 205 is such that the air flow within the chamber 202 is generally tangential. The effect of this air flow within the chamber 202 is to cause a medicament container 206 similar to either of the two embodiments described above to rotate around the chamber 202, as indicated by the larger curved arrow in FIG. 4. In undergoing this motion, the container 206 "hugs" the wall of the chamber 202. At the same time, the container 206 rotates about its own axis, as indicated by the smaller curved arrow. The container 206 thus undergoes an epicyclic motion, constrained by the wall of the chamber 202 while simultaneously spinning about its own axis.

As indicated by the short arrows in FIG. 4, medicament powder is dispensed from the container 206, under the influence of centrifugal forces, via the dispensing openings (not visible in FIG. 4) and in substantially all directions.

Medicament powder is dispensed simultaneously from both compartments in the container 206, the two medicaments becoming entrained and intimately mixed in the swirling airflow inhaled by the patient.

Figure 5:
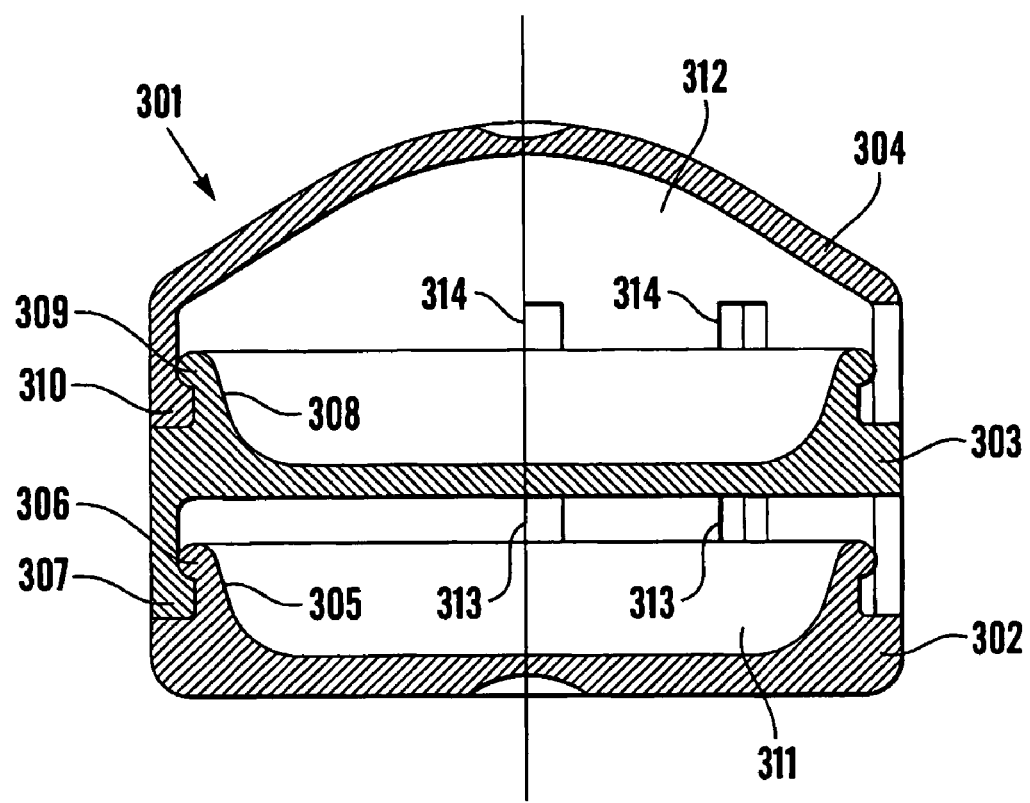
FIG. 5 is a sectional view of a third embodiment of a medicament container according to the invention.

Finally, FIG. 5 shows a third embodiment of a medicament container 301 according to the invention. This comprises three interfitting components 302, 303, 304, each of which is injection-moulded in plastics material. The lowermost (as viewed in FIG. 5) component 302 has the form of a shallow, flat-bottomed bowl, having an upstanding rim 305 which has an externally-extending peripheral lip 306. The intermediate component 303 is formed with a downwardly-depending skirt 307 that engages over the lip 306 with a snap fit. The upper part of the intermediate component 303 is formed as a shallow bowl, similar in form to that defined by the lowermost component 302, again having an upstanding rim 308 with a lip 309. The topmost component 304 is domed, with a peripheral skirt 310 that engages with a snap fit over the rim 308 and lip 309 of the intermediate component.

The lowermost component 302 and the intermediate component 303 between them define a first chamber 311, and the intermediate component 303 and the topmost component 304 define a second chamber 312. Series of openings 313,314 (only some of which are shown in FIG. 5) are formed respectively in the intermediate component 303 and the topmost component 304 to permit, in use, egress of medicament from the respective chambers 311,312.

It will be noted that the internal lower surfaces of the chambers 311,312 are curved. This arrangement serves to guide medicament within the chambers 311,312 towards the respective openings 313,314 under the influence of centrifugal forces, and hence facilitates dispensing of medicament from the chambers 311,312.

The invention claimed is:

1. A medicament container comprising at least two compartments, each of said compartments being adapted to contain a dose of a medicament in powdered form and each compartment being provided with at least one opening through which, in use, said medicament can be dispensed, the medicament container being arranged to allow doses of medicament contained in two or more compartments to be dispensed simultaneously wherein a user inhaling though a delivery device causes rotation of the container about an axis to dispense the medicament though the opening, wherein the container has a circular or substantially circular cross-section, and the container is pre-loaded with the doses of medicament, in a packaging which seals the openings until the medicament container is removed from the packaging and introduced into the delivery device for use.

2. A medicament container according to claim 1, wherein the diameter of the circular or substantially circular cross-section is greater than the depth of the container.

3. A medicament container according to claim 1, wherein the container is generally cylindrical in shape.

4. A medicament container according to claim 3, wherein one or both ends of the cylinder are convex or concave.

5. A medicament container according to claim 4, wherein at least one end of the container is substantially flat.

6. A medicament container according to claim 3, wherein the compartments are disposed one above the other, along a longitudinal axis of the container.

7. A medicament container according to claim 1, wherein the container comprises a plurality of compartments arranged as segments of a cylindrical disc.

8. A medicament container according to claim 7, wherein the container takes the form of a cylindrical drum divided by a diametral wall into two hemicylindrical compartments.

9. A medicament container according to claim 1, wherein the dispensing apertures are formed around the periphery of the compartments.

10. A medicament container according to claim 1, wherein each compartment has a plurality of apertures.

11. A medicament container according to claim 10 wherein the apertures of each compartment are equiangularly spaced around the wall of the compartment.

12. A medicament container according to claim 1, wherein the dispensing apertures are all of equal size.

13. A medicament container according to claim 1, wherein the dispensing apertures in different compartments are of different sizes.

14. A medicament container according to claim 1, wherein the container is manufactured from materials that are impermeable or substantially impermeable to moisture.

15. A medicament container according to claim 1, wherein the container comprises two compartments.

16. A medicament container according to claim 1, wherein more than one compartment contains the same medicament.

17. A medicament container according to claim 16, wherein two or more compartments contain the same medicament, but formulated differently.

18. A medicament container according to claim 17, wherein two or more compartments contain the same medicament, but having different particle size distributions.

19. A medicament container according to claim 1, wherein the container contains a combination of medicaments incorporated into separate compartments.

20. A medicament container according to claim 19, wherein the combination of medicaments comprises a bronchodilator ($\beta_2$-agonist) and a steroid.

21. A medicament container according to claim 20, wherein the combination of bronchodilator ($\beta_2$-agonist) and steroid is selected from the group consisting of: formoterol and budesonide; salmeterol and fluticasone; formoterol and fluticasone; and salmeterol and budesonide.

22. A medicament container according to claim 21, wherein the combination of anticholinergic and steroid is selected from the group consisting of: ipratropium bromide and budesonide; ipratropium bromide and fluticasone; oxitropium bromide and budesonide; and oxitropium bromide and fluticasone.

23. A medicament container according to claim 19, wherein the combination of medicaments comprises an anticholinergic and a steroid.

24. A medicament container according to claim 19, wherein the combination of medicaments comprises an anti-inflammatory drug (NSAID) and a steroid or an anti-cholinergic.

25. A medicament container according to claim 24, wherein the combination of anti-inflammatory drug (NSAID) and steroid or anti-cholinergic is selected from the group consisting of: sodium cromoglycate and budesonide; sodium cromoglycate and fluticasone; sodium cromoglycate and ipratropium bromide; sodium cromoglycate and oxitropium bromide; nedocromil sodium and budesonide; nedocromil sodium and fluticasone: nedocromil sodium and ipratropium bromide; and nedocromil sodium and oxitropium bromide.

26. A medicament container according to claim 19, wherein the combination of medicaments comprises a normal-acting and a long-acting formulation of the same active ingredient.

27. A medicament container according to claim 26, wherein the active ingredient is selected from the group consisting of proteins and peptides.

28. A medicament container according to claim 27, wherein the active ingredient is an insulin formulation.

29. A medicament container comprising at least two compartments, each of the compartments adapted to contain a dose of a medicament in powdered form and each compartment being provided with at least one opening through which, in use, the medicament can be dispensed, the medicament container being arranged to allow doses of medicament contained in two or more compartments to be dispensed simultaneously wherein a user inhaling though a delivery device causes rotation of the container about an axis to dispense the medicament though the opening, wherein the container is pre-loaded with the doses of medicament in a packaging which seals the openings until the medicament container is removed from the packaging and introduced into the delivery device for use.

* * * * *

Disclaimer

7,281,539 — Brindra Paul Singh Chawla, Nottingham (GB). MEDICAMENT CONTAINER. Patent dated October 16, 2007. Disclaimer filed January 18, 2008, by the assignee, Technology Innovation Limited.
The term of this patent shall not extend beyond the expiration date of Pat. No. 6,418,926.
*(Official Gazette, May 27, 2008)*